United States Patent [19]

Bernstein et al.

[11] Patent Number: 4,790,825
[45] Date of Patent: Dec. 13, 1988

[54] CLOSED CHEST CANNULATION METHOD AND DEVICE FOR ATRIAL-MAJOR ARTERY BYPASS

[75] Inventors: Robert I. Bernstein, Tenafly; Bernard Ackerman, Metuchen, both of N.J.

[73] Assignee: Electro Catheter Corporation, Rahway, N.J.

[21] Appl. No.: 904,336

[22] Filed: Sep. 5, 1986

[51] Int. Cl.⁴ .............................................. A61M 5/18
[52] U.S. Cl. .................................... 604/170; 604/165; 604/280; 128/657; 128/772
[58] Field of Search ........................................ 604/4-6, 604/51-53, 164-170, 280-284, 105, 110; 128/656-658, 772, 341, 343, 345

[56] References Cited

U.S. PATENT DOCUMENTS

| 2,221,138 | 11/1940 | Hendrickson | 128/341 |
| 3,674,033 | 7/1972 | Powers | 604/264 |
| 3,867,945 | 2/1975 | Long | 604/170 |
| 4,148,319 | 4/1979 | Kasper et al. | 604/170 |
| 4,273,131 | 6/1981 | Olsen | 128/341 |
| 4,509,945 | 4/1985 | Kramann et al. | 128/657 |

FOREIGN PATENT DOCUMENTS 0885917  8/1953  Fed. Rep. of Germany ...... 604/170

OTHER PUBLICATIONS

Cope; "Technique for Transeptal Catheterization of the Left Atrium"; Jour. of Thor. Med.; vol. 37, No. 4; pp. 482-486; 4/59.

Brockenbrough et al., "A New Technic for Left Ventricular Angiocardiography . . . ;" Am. Jour. of Card., pp. 1062-1064; 12/60.

Glassman et al.; "A Method of Closed Chest Cannulation of the Left Atrium . . . "; 69, Jour. of Thor. and Card. Surg., 283; 2/75.

Primary Examiner—Stephen C. Pellegrino
Assistant Examiner—Mario Costantino
Attorney, Agent, or Firm—Cohen, Pontani & Lieberman

[57] ABSTRACT

This method and device permits removal of venous blood from either atrium to a heart lung machine and thereafter returns it (after oxygenation and filtration if needed) to the femoral artery, all in a percutaneous mode. The device includes in combination a guide wire, catheter, transseptal needle, blunt internal obturator approximately the same length as the catheter with a circular barb to secure the catheter in a given longitudinal relationship, an external obturator about the same length as the internal obturator and removably attached thereto, a cannula for passage over the combined obturators and catheter and connectors to attach the cannula to an extracorporeal pump (and oxygenator if needed), which in turn can be connected to the arterial side of a patient's vascular system.

4 Claims, 2 Drawing Sheets

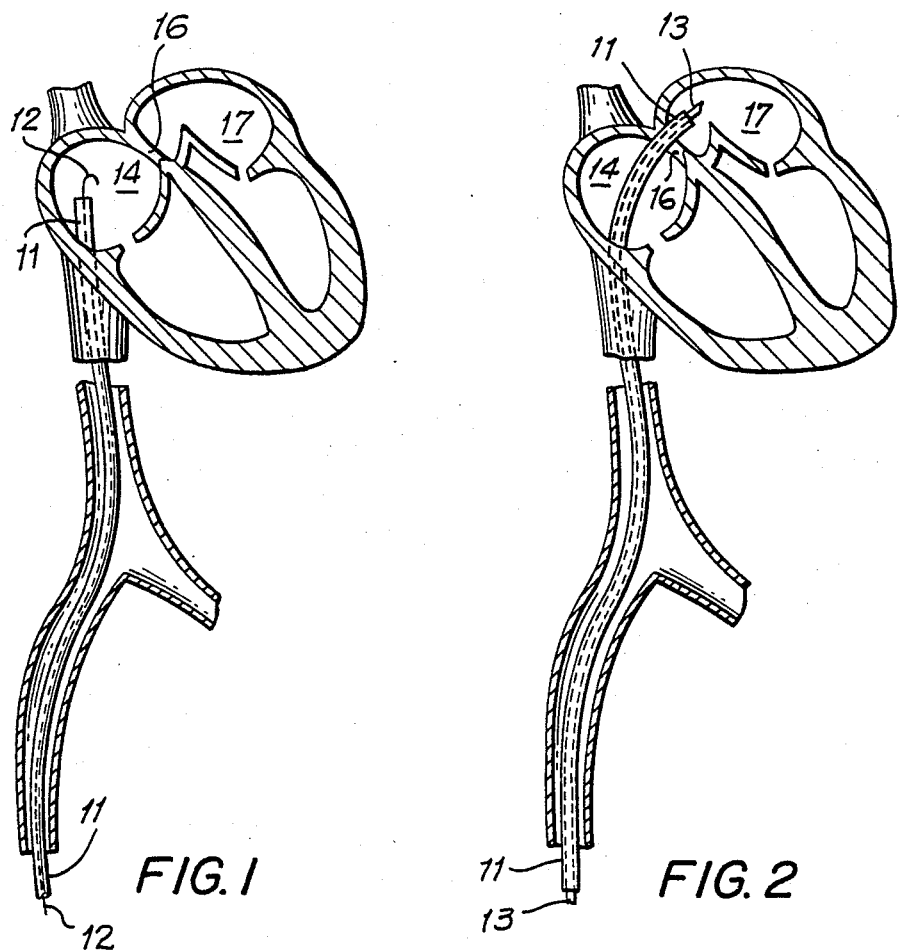

U.S. Patent    Dec. 13, 1988    Sheet 2 of 2    4,790,825
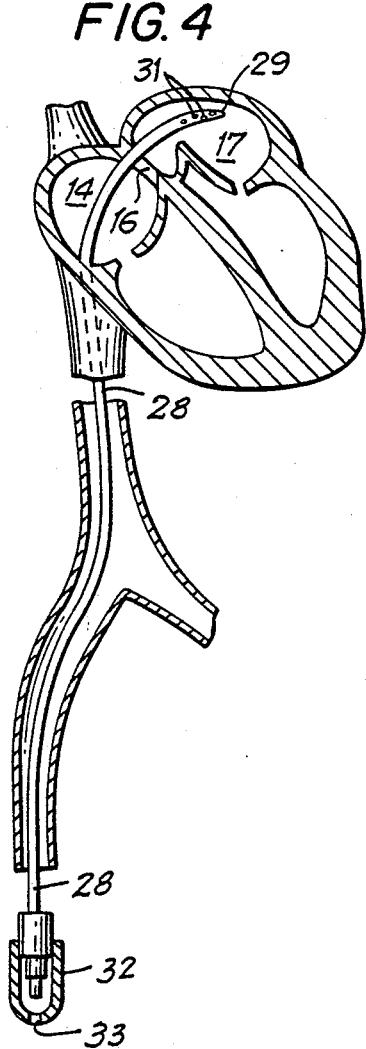
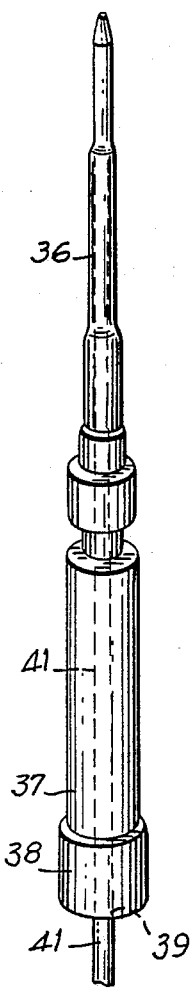

CLOSED CHEST CANNULATION METHOD AND DEVICE FOR ATRIAL-MAJOR ARTERY BYPASS

BACKGROUND OF THE INVENTION

This invention relates to new and useful improvements in percutaneous heart bypasses and more particularly seeks to provide a system that can be readily available for temporary or emergency cannulation procedures that does not require surgical intervention or personnel. The method involves essentially cannulae connections to the atria and a femoral or iliac artery or aorta by non-surgical personnel and avoids the complications of open heart surgery.

FIELD OF THE INVENTION

The primary field of this invention is medicine as it relates to assisting or taking the place of cardiac output of a weakened or diseased heart and particularly during heart surgery, trauma periods accompanying infarction or other heart damage, various other procedures, such as angioplasty, or waiting for a suitably matched transplant.

PRIOR ART

Since the advent of the heart-lung machine, which permits long periods of open-heart surgery, many new surgical techniques have been developed, including internal heart and heart valve repair, coronary artery bypass, natural and artificial heart transplant, etc. During surgical procedures, after heart attacks or to supplement chronically weakened hearts, procedures have been developed to assist or take over entirely the circulation of the blood through the patient's body by partial or complete bypass of the heart.

For temporary and particularly emergency problems such as surgery, evolving infarction treatment, or holding a potential transplant patient until a natural heart is available, there is a need for simple equipment in a hospital that can be quickly connected to the patient without surgical intervention and that can provide bypass time to the patient.

Moreover, when a patient is being treated for an evolving myocardial infarction, there is a need to relieve the heart of its work load to the maximum possible extent as quickly as possible. In this emergency situation, surgical intervention may be avoided if it is possible to quickly bypass and thus unload the heart work.

An earlier attempt and device to acomplish these results was described at 69 Journal of Thoracic and Cardiovascular Surgery 283 (Feb., 1975).

SUMMARY OF THE INVENTION

The invention comprises a method and device to cannulate the natural heart during emergency periods with the only connection with the patient being through cannulae connected to the atrial and arterial sides of the circulatory system. During intermediate steps, an internal blunt obturator and associated catheter are sized relative to each other for proper introduction and securement to assure that the catheter remains in its intended location. This permits more rapid and appropriate response to patients' conditions and is readily adaptable to be available and useable from a portable hospital cart without surgical intervention or jeopardy to the patient.

The device herein is preferably used in conjunction with the External Pulsatile Cardiac Assist Device described in copending application, Ser. No. 796,887 but also with other cardiac assist devices.

Further to the summary of this invention, the specific nature of which will be more apparent, the invention will be more fully understood by reference to the drawings, the accompanying detailed description and the appended claims.

BRIEF DRAWING DESCRIPTION

FIG. 1 is a diagrammatic sectional view showing a spring guide and catheter introduced through the femoral vein into the right atrium in accordance with this invention;

FIG. 2 is a diagrammatic sectional view of the transseptal needle and catheter having advanced through the atrial septum;

FIG. 3 is a cross-sectional exploded view of the obturators;

FIG. 4 is a diagrammatic sectional view of the cannula when positioned in the left atrium; and FIG. 5 is a perspective view of the arterial cannula and dilator.

DESCRIPTION OF THE PREFERRED EMBODIMENTS

A cannula is inserted in the right femoral vein and passed to the right or left atrium to take blood. If taken from the left atrium, the oxygenator (not shown) may be excluded or bypassed, as the lungs will be functioning. A roller pump with approximately 80-100 mm Hg suction is used to remove the blood from either atria.

The blood is passed through or around the oxygenator and goes to a pump chamber (not shown) and then back to the arterial side at the left or right femoral artery or the cannula may be extended past the bifurcation into the abdominal aorta.

This circulation from the roller pump back to the arterial side obviously completes the circuit but is not considered part of the present invention.

An inguinal incision isolates the junction of the right saphenous and femoral veins, through which a No. 9 French (69 cm long) polyethylene radiopaque catheter 11 is inserted and passed into the right atrium under fluoroscopic control with a Seldinger guide wire 12 as an introducer. The guide wire 12 is removed and a 70 cm, 17 gauge Ross transseptal needle 13 inserted through the lumen of catheter 11 and extending slightly beyond the catheter tip. The needle is advanced into the right atrium 14 and with constant pressure and fluoroscopic monitoring, the atrial septum 16 is punctured in the fossa ovalis area. The No. 9F catheter 11 is then advanced through the atrial septum 16 over the Ross needle 13 tip approximately 4 cm into the left atrium 17 and the Ross needle removed. The needle is replaced by an internal obturator 18 having a blunt curved distal end 19 and an externally threaded proximal end 21. Adjacent the externally threaded proximal end 21 of obturator 18 and extending in a distal direction away therefrom is an enlarged section 22, an intermediate offset enlarged section 23 and a circular barb 24. The internal obturator 18 and catheter 11 have relative lengths such that the blunt end 19 terminates about 1 cm proximally of the catheter distal tip when the proximal catheter end is fitted snugly over the circular barb 24 and against the enlarged portion 22. The circular barb 24 over which catheter 11 is secured in the appropriate longitudinal relationship is important. Other means to secure the catheter may be used such as an internal flange on the proximal end that would be clamped between the internal and external obturators when they are threaded together. The enlarged portion 22 which stops the advance of the proximal end of catheter 11 has the same outside diameter as the external obturator 26 which is internally threaded at its distal end 27 to mate evenly with the internal obturator. The blunt end 19 of the internal obturator, which is proximal to the catheter 11 tip, is advanced into the left atrium.

A 27F, 69 cm cannula 28 is then passed over the external obturator 26 and catheter 11 which encloses the internal obturator 18 until the tapered tip 29 having side holes 31 is positioned within the left atrium 17. The obturators 18, 26 and the catheter 11 is then removed through cannula cap 32 and hole 33. The cannula is at least partially radiopaque by stripes or otherwise to follow its course under the fluoroscope. The location of side holes 31 can be determined by withdrawal of blood which will be bright red (oxygenated) from the left atrium 17 and dark red from the right atrium 14. The proximal end of cannula 28 is now ready for connection to an extracorporeal pump unit (not shown) or to be clamped.

A cut down is performed on the right femoral artery into which a 21F, 12.5 cm arterial cannula 36 which has a blood line connector 37 and protective cap 38 with hole 39. A 17F, 50.5 cm arterial dilator 41 is inserted through hole 39. After extension of the dilator to the desired location in the femoral artery or upstream to the iliac or aorta, the dilator is removed and the cannula connected to the pump or clamped.

Entry herein has been shown at the most common entry site, the femoral vein but other accessible veins large enough for cannula 28 may be used such as the subclavian, axillary or internal jugular.

We claim:

1. An obturator device for facilitating the introduction of a cannula into the left ventricle of a patient's heart via the aortic valve using a trans-arterial insertion technique wherein the cannula is passed over a catheter having an outside diameter which substantially corresponds to the inside diameter of the cannula and a length and which catheter has been previously inserted into the left ventricle, said device comprising:

an internal obturator for insertion into the catheter to stiffen same whereby the internal obturator and catheter, together, may be used as a guide to facilitate introduction of the cannula into the left ventricle, said internal obturator having a proximal end and a distal end, with the distal end terminating in a blunt curved portion to facilitate passage of the internal obturator through tortuous segments of the patient's arterial system as it is passed to the left ventricle, and wherein the proximal end of the internal obturator terminates in an enlarged section having an outside diameter substantially corresponding to the outside diameter of the catheter, whereby, when said internal obturator is inserted into the catheter and the enlarged section of said internal obturator is brought into abutting relation with the catheter, there results a substantially continuous uniform outside diameter traveling from the enlarged section of said internal obturator to the catheter so that the cannula may easily pass from the enlarged portion of said internal obturator to the catheter with a minimum of interference, said internal obturator further including a circular barb located between the enlarged section at the proximal end and the blunt curved portion at the distal end for retaining the catheter in abutting relation with the enlarged section during insertion of the cannula and subsequent removal of the catheter together with said internal obturator following cannula insertion, and wherein, said internal obturator has a length relative to the catheter length so that when said internal obturator is inserted in the catheter, the blunt curved portion terminates within the catheter about 1 centimeter before the catheter itself terminates within the patient's left ventricle;

said device further comprising an external obturator having an external diameter which substantially corresponds to the external diameter of the enlarged section of said internal obturator for passage of the cannula thereover; and releasable attachment means for releasably attaching the external obturator to the proximal end of the internal obturator.

2. The obturator device according to claim 1, wherein the circular barb is located adjacent to the proximal end of the internal obturator.

3. The obturator device according to claim 1, wherein said releasable attachment means comprises corresponding male and female threads located, respectively, in the proximal end of said internal obturator and in said external obturator.

4. The obturator device according to claim 2, wherein said releasable attachment means comprises corresponding male and female threads located, respectively, in the proximal end of said internal obturator and in said external obturator.

* * * * *